United States Patent [19]

Ghahramani

[11] 4,151,743

[45] May 1, 1979

[54] DENSITOMETER DRIVE

[75] Inventor: Iraj Ghahramani, Los Angeles, Calif.

[73] Assignee: International Telephone and Telegraph Corporation, New York, N.Y.

[21] Appl. No.: 919,967

[22] Filed: Jun. 28, 1978

[51] Int. Cl.² ............................................. G01N 9/00
[52] U.S. Cl. .................................................. 73/32 A
[58] Field of Search .............................. 73/32 A, 32 R

[56] References Cited

U.S. PATENT DOCUMENTS 3,967,490   7/1976   Brady ................................. 73/32 A Primary Examiner—James J. Gill
Attorney, Agent, or Firm—A. Donald Stolzy

[57] ABSTRACT

A vibration densitometer having a magnetostrictive drive with a coil, and a crystal pick-up. A loop circuit including a driver amplifier provides the coil with current which leads the crystal voltage by 90 degrees for maximum efficiency.

2 Claims, 4 Drawing Figures

4,151,743

DENSITOMETER DRIVE

BACKGROUND OF THE INVENTION

This invention relates to a vibration densitometer, and more particularly to a magnetostrictive current drive therefor having a phase leading the pick-off signal by 90 degrees.

In the past, densitometers have been inefficient because they have employed combination voltage and current drives of various phases.

PRIOR ART STATEMENT

Combination voltage and current drives of various phases are disclosed in U.S. Pat. No. 3,878,374 issued Apr. 15, 1975.

A permanent magnet biased 90 degree leading current drive is disclosed in copending application of a prior invention Ser. No. 837,454, filed Sept. 28, 1977, by P. Z. KALOTAY and I. GHAHRAMANI for DENSITOMETER.

SUMMARY OF THE INVENTION

In accordance with the present invention, the above-described and other disadvantages of the prior art are overcome by providing a vibration densitometer comprising: a probe having input and output leads; a loop circuit having an input lead, and first and second output leads, said first output lead being connected to said probe input lead; a function generator connected from said second output lead; utilization means connected from said function generator, said probe having a vibratable member and a magnetostrictive driver including a coil to vibrate said member, said loop circuit including a differential amplifier having inverting and noninverting inputs, an output, and a summing junction connected to said inverting input, a negative source of potential, means including a first resistor connected to said inverting input to provide an input to said amplifier, a second resistor connected from said source to said junction, a third resistor, a fourth resistor, said coil having one end connected from said amplifier output and another end, said noninverting input being connected to a point of reference potential, said fourth resistor having a resistance $R_4$, said third resistor having a resistance $R_3$ such that $R_3 \gg R_4$, said fourth resistor being connected from said other coil end at a mutual junction to said point of reference potential, said third resistor being connected from said mutual junction to said summing junction, said loop circuit having a phase circuit adjusted to hold the current in said coil 90 degrees leading the vibration of said member, and a capacitor connected directly from said one coil end to said summing junction.

The above-described and other advantages of the present invention will be better understood from the following detailed description when considered in connection with the accompanying drawings.

BRIEF DESCRIPTION OF THE DRAWINGS

In the drawings which are to be regarded as merely illustrative.

DESCRIPTION OF THE PREFERRED EMBODIMENT

Figure 1:
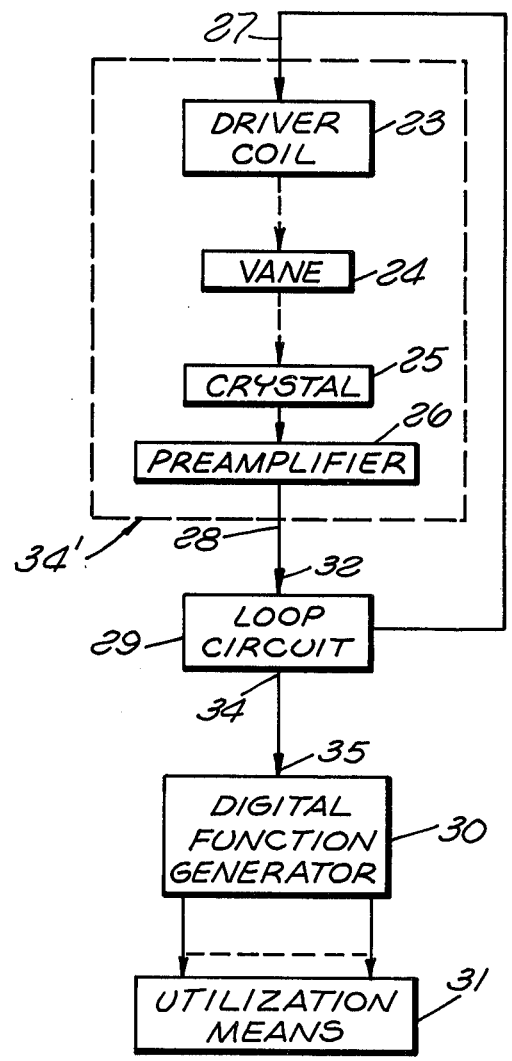
FIG. 1 is a block diagram of a vibration densitometer.

In the drawings, in FIG. 1, a vibration densitometer probe is indicated at 34' having a driver coil 23, a vane 24, a piezoelectric crystal 25 and a preamplifier 26.

Probe 34' has an input lead 27 and an output lead 28.

Other blocks shown in FIG. 1 are a loop circuit 29, a digital function generator 30 and utilization means 31. Loop circuit 29 has an input lead 32 connected from probe output lead 28, and output leads 33 and 34. Digital function generator 30 has an input leads 35 connected from loop circuit output lead 34. The output of digital function generator 30 is connected to utilization means 31.

The input lead 27 of probe 34' is connected from the output lead 33 of loop circuit 29. Probe 34' and loop circuit 29 form a closed loop electromechanical oscillator. Vane 24 is submerged in a fluid. The density of the fluid is a function of the frequency at which vane 24 vibrates.

Digital function generator 30 may have its input lead 35 connected from lead 33 or at other points in loop circuit 29. Loop circuit 29 impresses a square wave voltage on input lead 35 of digital function generator 30.

Utilization means 31 shown in FIG. 1 may be a density indicator, a specific gravity indicator, a process controller or otherwise.

The disclosures of the following patents are hereby incorporated herein:

(1) U.S. Pat. No. 3,677,067, issued July 18, 1972.
(2) U.S. Pat. No. 3,706,220, issued Dec. 19, 1972.
(3) U.S. Pat. No. 3,738,155, issued June 12, 1973.
(4) U.S. Pat. No. 3,741,000, issued June 26, 1973.
(5) U.S. Pat. No. 3,878,374, issued Apr. 15, 1975.

Probe 34' shown in FIG. 1 may be conventional. For example, it may or may not be identical to that disclosed in U.S. Pat. No. 3,878,374. Alternatively, probe 34' may be similar to or identical to a probe shown in any of the patents above cited.

Probe 34', digital function generator 30 and utilization means 31 may be similar to or identical to corresponding ones in said U.S. Pat. No. 3,878,374. Loop circuit 29 is not.

Figure 2:
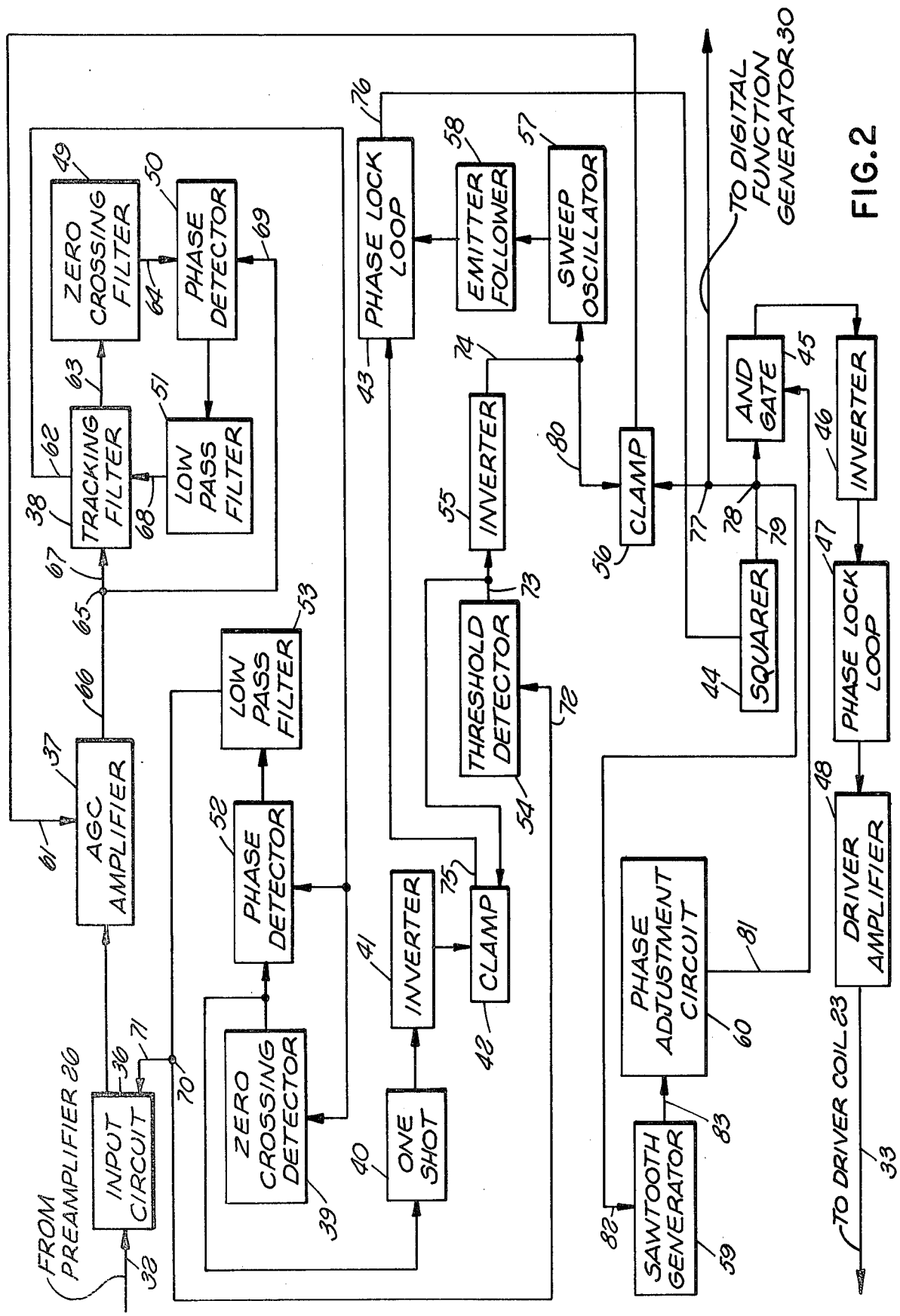
FIG. 2 is a detailed block diagram of a loop circuit shown in FIG. 1.

Loop circuit 29 is shown in FIG. 2 including an input circuit 36, an AGC amplifier 37, a tracking filter 38, a zero crossing detector 39, a one-shot multivibrator 40, an inverter 41, a clamp 42, a phase lock loop 43, a squarer 44, an AND gate 45, an inverter 46, a phase lock loop 47 and a driver amplifier 48 connected in succession as serial stages from input lead 32 of input circuit 36 to its output lead 33 and connected respectively from the output lead 28 of probe 34' and to the input lead 27 of probe 34'.

In FIG. 2, other stages are a zero crossing detector 49, a phase detector 50, a low pass filter 51, a phase detector 52, a low pass filter 53, a threshold detector 54, an inverter 55, a clamp 56, a sweep oscillator 57, an emitter-follower 58, a saw-tooth generator 59 and a phase adjustment circuit 60.

AGC amplifier 37 has an AGC input lead 61 connected from the output of clamp 56.

Tracking filter 38 has two output leads 62 and 63. Tracking filter output lead 63 is connected to the input of zero crossing detector 49. The output of zero crossing detector 49 is connected to one input 64 of phase detector 50. A junction is provided at 65 from which an output lead 66 of AGC amplifier 37 is connected. Tracking filter 38 has two input leads 67 and 68. Tracking filter input lead 67 is connected from junction 65.

Phase detector 50 has a second input lead 69 connected from junction 65. The output of phase detector 50 is connected to the input of low pass filter 51. The output of low pass filter 51 is connected to the input lead 68 of tracking filter 38.

The purpose of zero crossing detector 49, phase detector 50 and low pass filter 51 is to cause tracking filter 38 to track the frequency of output signal of AGC amplifier 37. The signal on the tracking filter input lead 68, thus, causes the passband thereof to straddle the frequency of the input to tracking filter 38 over input lead 67.

The output of tracking filter 38 on output lead 62 thereof is 90 degrees out of phase with the signal on the output lead 63 thereof. The signal from the tracking filter output lead 62 is impressed upon zero crossing detector 39 and phase detector 52. The output of zero crossing detector 39 is impressed both upon phase detector 52 and one-shot 40. The output of phase detector 52 is impressed upon low pass filter 53.

A junction is provided at 70 connected from the output of low pass filter 53. A lead 71 is connected from junction 70 to input circuit 36 to the AGC input of an amplifier therein for automatic gain control.

Threshold detector 54 has an input 72 connected from junction 70. Input lead 72 of threshold detector 54, when below a predetermined potential, causes the potential of the output lead 73 of threshold detector 54 to go either high or low. The output lead 73 of threshold detector 54 is, thus, for example, either ground or +15 volts, as defined hereinafter. When the output of low pass filter 53 is below the predetermined potential, output lead 73 of threshold detector 54 is at ground.

Threshold detector 54 operates both of the clamps 42 and 56 and the sweep oscillator 57. Clamp 56 and sweep oscillator 57 are operated through the inverter 55.

Inverter 55 has an output lead 74 which also assumes potentials of +15 volts or ground.

Clamp 42 either passes the output of inverter 41 to the phase lock loop 43 or in the other state of the threshold detector 54, clamp 42 having an output lead 75, is operated to clamp the output lead 75 to ground. The output of inverter 55 is simply the reverse of the output detector 54. When the output of inverter 55 is high, sweep oscillator 57 receivers power. When the output of inverter 55 is low, the output of sweep oscillator 57 is at ground.

Emitter follower 58 is connected between sweep oscillator 57 and phase lock loop 43. Phase lock loop 43 has an output lead 76 which is connected to squarer 44. Junctions are provided at 77 and 78. Squarer 44 has an output lead 79 connected to junction 78. Junction 78 is connected to junction 77. Clamp 56 is connected from junction 77 to AGC amplifier input lead 61.

When the output of threshold detector 54 is high, loop circuit 29 is tracking and opens clamp 42 to unground the output lead 75 thereof. Conversely, at the same time, inverter 55 grounds the input to sweep oscillator 57 and disables it. During tracking, inverter 55 also disables the output of clamp 56 by a connection 80 from inverter output lead 74 to clamp 56.

During searching, threshold detector 54 holds the output of clamp 42 at ground while inverter 55 operates sweep oscillator 57 and clamp 56 passes the output of squarer 44 to the AGC input lead 61 of AGC amplifier 37.

In FIG. 2, junction 77 is connected to digital function generator 30 shown in FIG. 1.

AND gate 45 receives an input from junction 78 and from an output lead 81 of phase adjustment circuit 60.

Saw-tooth generator 59 has an input lead 82 connected from junction 78, and an output lead 83 connected to an input of phase adjustment circuit 60.

Circuit 60 is manually adjustable to manually adjust the phase of the sine wave component of the current in coil 23 to be 90 degrees leading the output voltage of crystal 25. This adjustment makes the electromechanical oscillator oscillate with maximum efficiency.

OPERATION

In the embodiment of the invention shown in FIG. 1, probe 34' and loop circuit 29 provide an electromechanical oscillator which oscillates at a frequency dependent upon the density of the fluid in which vane 24 is immersed. The same is true of the pulse repetition frequency of the square wave voltage applied to the input lead 35 of digital function generator 30.

For more details of the operation, see U.S. Pat. No. 3,878,374.

Digital function generator 30 may be described as a digital linearization circuit. It produces a digital output directly proportional to density from the input signal thereto impressed upon the input lead 35 thereto.

All of the blocks shown in FIG. 2 may be entirely conventional as disclosed in U.S. Pat. No. 3,878,374, except driver amplifier 48.

Figure 3:
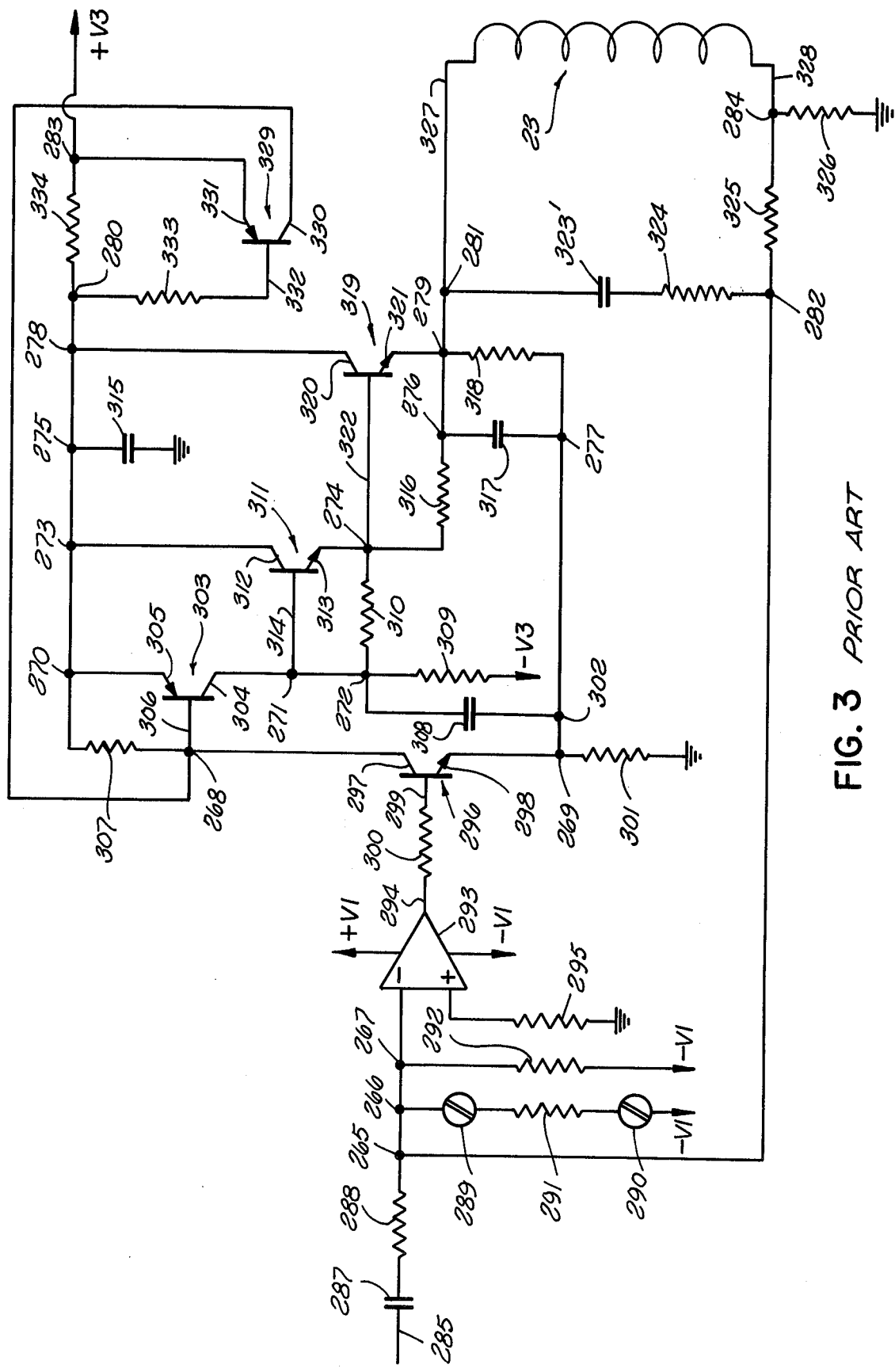
FIG. 3 is a schematic diagram of a prior art driver amplifier.
Figure 4:
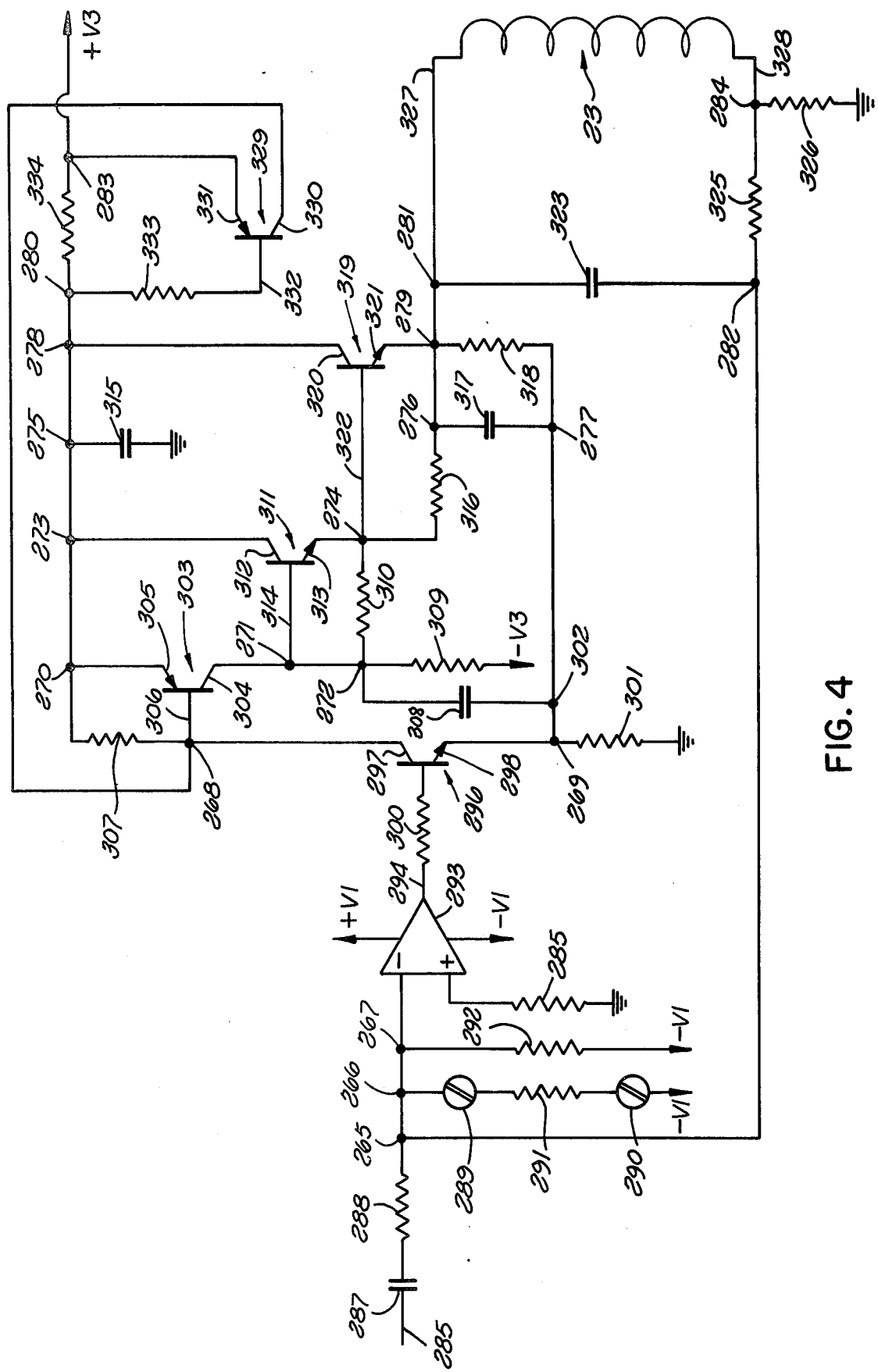
FIG. 4 is a schematic diagram of the driver amplifier of the present invention.

A driver amplifier disclosed in the last-mentioned patent is shown in FIG. 3. Driver amplifier 48 of the present invention is shown in FIG. 4. FIG. 4 is identical to FIG. 3 except that resistor 324 in FIG. 3 is short circuited in FIG. 4, and, in FIG. 4, capacitor 323 is very small. Typically capacitor 323 in FIG. 4 is 10 nanofarads (to flatten the gain versus frequency curve).

The prior art driver amplifier is shown in FIG. 3. In FIG. 3, various junctions are illustrated at 265, 266, 267, 268, 269, 270, 271, 272, 273, 274, 275, 276, 277, 278, 279, 280, 281, 282, 283 and 284. (Other junctions are not mentioned here.)

The prior art driver amplifier has an input lead 285.

In FIG. 3, a capacitor 287 and a "first" resistor 288 are connected in series in that order from lead 285 to junction 265.

Symbols at 289 and 290 indicate that a resistor 291 may be replaced between junction 266 and potential −V1. A "second" resistor 292 is connected between junction 267 and potential −V1. Junction 267 is called a "summing junction" as is conventional with an analog adder-subtractor. Junctions 265, 266 and 267 are connected together. A differential amplifier 293 is provided with an output lead 294. Amplifier 293 has an inverting input lead connected from junction 267. A resistor 295 (sometimes optional) is connected from the non-inverting input lead of amplifier 293 to ground. A transistor 296 is provided having a collector 297, an emitter 298 and a base 299. A resistor 300 is connected from amplifier output lead 294 to base 299. Emitter 298 is connected to junction 269. A resistor 301 is connected from junction 269 to ground. A junction 302 is connected from junction 269. A junction 277 is connected from junction 302.

Collector 297 is connected to a junction 268. A transistor is provided at 303 having a collector 304, an emitter 305 and a base 306. Base 306 is connected from junction 268. Emitter 305 is connected from junction 270. Collector 304 is connected to junction 271. Junctions 271 and 272 are connected together. A resistor 307 is connected between junctions 268 and 270. A capacitor 308 is connected between junctions 272 and 302. A resistor 309 is connected from junction 272 to potential −V3. A resistor 310 is connected between junctions 272 and 274. A transistor 311 is illustrated having a collector 312, an emitter 313 and a base 314. Base 314 is connected from junction 271. Collector 312 is connected from junction 273. Emitter 313 is connected to junction 274. Junctions 270, 273, 275, 278 and 280 are all connected together.

A transistor 319 is provided having a collector 320, an emitter 321 and a base 322. Base 322 is connected from junction 274. Collector 320 is connected from junction 278. Emitter 321 is connected to junction 279. A capacitor 323′ and a resistor 324 are connected in series in that order from junction 281 and junction 282. A "third" resistor 325 is connected between "mutual junction" 284 and junction 282. A "fourth" resistor 326 is connected from junction 284 to ground.

As shown in FIG. 3, driver coil 23 has leads 327 and 328 connected to junctions 281 and 284, respectively.

A transistor 329 is provided in FIG. 3 including a collector 330, an emitter 331 and a base 332. A resistor 333 is connected from junction 280 to base 332. A resistor 334 is connected between junctions 280 and 283. Emitter 331 is connected from junction 283. Collector 330 is connected to junction 268. Junction 282 is connected to junction 265.

In FIG. 4, the current drive (the addition of the small capacitor 323 and the removal of resistor 324—see FIG. 3) makes the densitometer drive very efficient.

The following terms are hereby defined:
(1) I coil AC is the A.C. current in the coil 23;
(2) $R_5$ is the resistance of resistor 291;
(3) $V_{in}$ is the potential (constant A.C.) on lead 285;
(4) I coil DC is the D.C. current in the coil 23;
(5) I coil =I coil AC +I coil DC;
(6) $R_1$ is the resistance of resistor 288;
(7) $R_2$ is the resistance of resistor 292;
(8) $R_3$ is the resistance of resistor 325; and
(9) $R_4$ is the resistance of resistor 326.

The formulas are $$\text{I coil DC} = \left[ \frac{V_1 (R_2 + R_5)}{R_2 R_5} \right] \left[ \frac{R_3}{R_4} \right]$$

$$\text{I coil Ac} = \frac{V_{in} R_3}{R_1 R_4}$$

The A.C. current in coil 23 is a fixed amplitude current.

What is claimed is:

1. A vibration densitometer comprising: a probe having input and output leads; a loop circuit having an input lead, and first and second output leads, said first output lead being connected to said probe input lead; a function generator connected from said second output lead; utilization means connected from said function generator, said probe having a vibratable member and a magnetostrictive driver including a coil to vibrate said member, said loop circuit including a differential amplifier having inverting and noninverting inputs, an output, and a summing junction connected to said inverting input, a negative source of potential, means including a first resistor connected to said inverting input to provide an input to said amplifier, a second resistor connected from said source to said junction, a third resistor, a fourth resistor, said coil having one end connected from said amplifier output and another end, said noninverting input being connected to a point of reference potential, said fourth resistor having a resistance $R_4$, said third resistor having a resistance $R_3$ such that $R_3 > > R_4$, said fourth resistor being connected from said other coil end at a mutual junction to said point of reference potential, said third resistor being connected from said mutual junction to said summing junction, said loop circuit having a phase circuit adjusted to hold the current in said coil 90 degrees leading the vibration of said member, and a capacitor connected directly from said one coil end to said summing junction.

2. The invention as defined in claim 1, wherein the output voltage of said probe lags the current in said coil by 90 degrees.

* * * * *